US000001903H

United States Statutory Invention Registration [19]

[11] Reg. Number: H1,903

Bowden et al. [45] Published: Oct. 3, 2000

[54] ISOLATED HAIR KERATIN GENES AND THEIR USE IN HAIR GROWTH ACTIVE IDENTIFICATION ASSAYS

[75] Inventors: Paul Edward Bowden, South Glamorgan, United Kingdom; Xiaochun Luo, West Chester; Cynthia Jo. Wawrzyniak, Sharonville, both of Ohio

[73] Assignee: The Procter & Gamble Company, Cincinnati, Ohio

[21] Appl. No.: 08/117,373

[22] Filed: Sep. 2, 1993

Related U.S. Application Data

[63] Continuation-in-part of application No. 07/960,984, Oct. 13, 1992, abandoned, which is a continuation-in-part of application No. 07/783,604, Oct. 25, 1991, abandoned.

[51] Int. Cl.[7] ..... C07H 17/00

[52] U.S. Cl. ..... 536/23.5

[58] Field of Search ..... 435/6, 91.2; 935/77, 935/78

*Primary Examiner*—Donald P. Walsh
*Assistant Examiner*—Anthony R. Chi
*Attorney, Agent, or Firm*—Brahm J. Corstanje; David L. Suter; Jacobus C. Rasser

[57] ABSTRACT

The present invention relates to an isolated human hair specific keratin gene or fragment thereof, comprising a DNA sequence selected from the group consisting of SEQ ID NO:11; and a DNA sequence comprising DNA sequences SEQ ID NO:6, SEQ ID NO:7, SEQ ID NO:8, SEQ ID NO:9 and SEQ ID NO:10. The present invention also relates to a method for detecting the level of hair specific keratin in a biological sample. The present invention further relates to a method of identifying hair growth regulating compounds and compositions comprising: a) treating a subject with a compound or composition of interest; b) isolating a sample of hair from the subject; and c) using a DNA sequence, or fragment thereof, which encodes hair specific keratin as a marker in a biological assay to detect an increase in the production of hair specific keratin in the hair sample.

3 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ISOLATED HAIR KERATIN GENES AND THEIR USE IN HAIR GROWTH ACTIVE IDENTIFICATION ASSAYS

This is a continuation-in-part of application Ser. No. 07/960,984, filed on Oct. 13, 1992 now abandoned; which is a continuation-in-part of application Ser. No. 07/783,604, filed on Oct. 25, 2991 now abandoned.

TECHNICAL FIELD

This invention relates to the field of regulating hair growth, and specifically to isolated human hair keratin intermediate filament genes, or fragments thereof, useful as biological markers for identifying compounds useful for regulating hair growth.

BACKGROUND

Society in general continues to attach a stigma to hair loss. Men and women suffer from hair loss, often resulting in self-consciousness relating to the hair loss. Domestic animals, such as cats and dogs, also suffer from hair loss. While the animal is not likely to be emotionally affected by such hair loss, its owner may be, particularly if such an animal is to be shown in various competitions. Additionally, increased hair growth in livestock such as sheep, thereby resulting in increased wool production, is also desirable.

The desire for a healthy full head (or body, in the case of animals) of hair has resulted in a flurry of activity in the technical community to find compounds capable of inducing hair growth. Unfortunately, even the preliminary identification of compounds potentially useful for inducing hair growth is extremely time consuming. Currently, animal models which experience hair loss similar to humans are often used to identify useful compounds. Unfortunately, the researcher must frequently wait months or years for the animal to reach that stage in its life when it begins to lose hair. The researcher must then generally wait several more months following treatment with a compound of interest before assessing the treated area to determine if hair growth has in fact occurred. Such waiting periods are a clear impediment to the search for hair growth actives.

For the foregoing reasons, there is a need for a marker useful for quickly, reliably, and noninvasively identifying whether hair growth is occurring in a subject, as well as a need for a quick, reliable, noninvasive assay employing such a marker for identifying potential hair growth regulating compounds and compositions.

Objects of the Present Invention

It is an object of the present invention to provide an isolated human hair specific keratin gene, or fragment thereof.

It is also an object of the present invention to provide a method for detecting the level of hair specific keratin in a biological sample.

It is also an object of the present invention to provide a method of identifying hair growth regulating compounds and compositions.

It is also an object of the present invention to provide a method for detecting the efficacy of a known hair growth regulating compound with respect to a subject being treated with the compound.

It is also an object of the present invention to provide a method for detecting hair loss.

SUMMARY

The present invention is drawn to isolated hair keratin intermediate filament genes which satisfy the need for a marker useful in a quick, dependable, and noninvasive assay for identifying potential hair growth regulating compounds and compositions.

In one embodiment of the present invention, the isolated hair specific keratin gene has the following DNA sequence: SEQ ID NO:11.

In another embodiment of the present invention, the isolated hair specific keratin gene has a DNA sequence comprising the following DNA sequences: SEQ ID NO:6, SEQ ID NO:7, SEQ ID NO:8, SEQ ID NO:9, and SEQ ID NO:10.

The present invention also relates to a method for detecting the level of hair specific keratin in a biological sample, the method comprising: a) isolating the biological sample from a subject; and b) using a DNA sequence or fragment thereof which encodes for hair specific keratin as a marker in a biological assay to detect the level of hair specific keratin in the biological sample.

The present invention further relates to a method of identifying hair growth regulating compounds and compositions comprising: a) treating a subject with a compound or composition of interest; b) isolating a sample of hair from the subject; and c) using a DNA sequence, or fragment thereof, which encodes for hair specific keratin as a marker in a biological assay to detect an increase in the production of hair specific keratin in the hair sample.

DETAILED DESCRIPTION

Hair specific keratin intermediate filament (IF) proteins are one of the major components of the hair shaft (the others being high-sulfur proteins, ultra-high sulfur proteins, and glycinetyrosine rich proteins). More than twenty species of the hair specific keratin IF proteins have been identified in different organs of the human body (Moll, R., W. Franke, D. Schiller, B. Geieger and R. Krepler, (1982) The Catalog of Human Cytokeratins: Patterns of Expression in Normal Epithelia, Tumor and Cultured Cells, Cell, Vol. 31, pp. 11–24), and eight species of hair specific keratin IF proteins are present in the hair shaft (Heid, H. W., I. Moll and W. W. Franke, (1988) "Patterns of Expression of Trichocytic and Epithelial Cytokeratins in Mammalian Tissues", *Differentiation,* Vol. 37, pp. 137–157).

The hair specific keratin IF proteins are produced by the trichocytes in the base (bulb) of the hair follicle. The process of hair specific keratin IF protein production is under tight regulation such that the hair specific keratin IF proteins are made at the appropriate site and appropriate time. This regulation of hair specific keratin IF protein production is primarily achieved by regulating the activation/inactivation of hair specific keratin gene expression. Activation of a hair specific keratin IF gene will result in an increase in production of its corresponding hair specific keratin IF protein, which, in turn, may result in an increase in hair shaft production. Therefore, activating hair specific keratin genes to produce hair specific keratin IF proteins will have a profound effect in stimulating hair shaft production. Any compounds which can do so are potentially useful for regulating hair growth. Identification of these compounds will be facilitated by isolation of one or more hair specific keratin IF genes.

The Applicants have determined that such an isolated hair specific keratin IF gene would be useful in a biological assay for identifying potential hair growth regulating compounds and compositions. The use of the hair specific keratin IF gene as a marker would have several advantages. The assay would have the advantage of reliability as hair specific keratin IF proteins are one of the major components of the hair shaft and measuring hair specific keratin IF RNA production would be a direct measurement of hair shaft formation. The assay would have the advantage of speed as an increase in hair specific keratin RNA production would occur much earlier (a few weeks) than an increase in hair shaft formation (several months) following treatment with a hair regulating compound. Lastly, the assay would have the advantage of noninvasiveness in that hair specific keratin RNA could be detected in a few plucked hairs without biopsying.

As used herein, "A", "T", "G", "C" and "U", refer to the nucleotides containing adenine, thymine, guanine, cytosine and uracil, respectively.

As used herein, "N" means an unknown nucleotide.

As used herein, "DNA" means deoxyribonucleic acid.

As used herein, "RNA" means ribonucleic acid.

As used herein, "gene" means a discreet segment of DNA of a chromosome, the segment of DNA being involved in producing RNA and/or one or more polypeptides.

As used herein, "regulating hair growth" means increasing the level of hair specific keratin RNA production, and/or inducing the formation of a greater number of hair strands, and/or increasing the diameter of the hair strand, and/or lengthening the hair strand, and/or converting the hair follicle from vellus to terminal, and/or preventing, retarding, or arresting the process of hair loss.

As used herein, "vellus hair follicle" means a hair follicle which produces a soft, short, and often colorless hair fiber. The size of the vellus follicle is considerably smaller than the terminal hair follicle. In an adult, vellus follicles can be found on the forehead, eyelids, and bald scalp.

As used herein, "terminal hair follicle" means a hair follicle which produces a coarse, long, and often pigmented hair follicle. The size of the terminal follicle is considerably larger than the vellus follicle. In the adult, the terminal follicles can be found on the scalp, axilla and pubic areas.

As used herein, "biological assay" means analyzing a sample for a biological substance of interest. For purposes of the present invention, the biological substance of interest is hair specific keratin RNA. Preferred biological assays include Northern Blotting Analysis, RNase Protection Assay, Dot Blotting Analysis, and Reverse Transcription-Polymerase Chain Reaction (RT-PCR); more preferably RT-PCR.

As used herein, "keratin" preferably refers to hair specific keratin intermediate filament.

As used herein, "subject" means animal or human, preferably human. Preferred animal subjects are rodents and simians. A preferred simian subject is the macaque. A preferred rodent subject is the mouse.

As used herein, "biological sample" preferably means hair strand, hair strands, or skin biopsies.

As used herein, "in vitro material" preferably means epithelial cells, hair follicle epithelial cells, hair follicle epithelial matrix cells, or hair follicle organ culture; more preferably hair follicle epithelial matrix cells.

As used herein, "comprising" means that other steps, ingredients, and/or base pairs which do not affect the end result can be added. This term encompasses the terms "consisting of" and "consisting essentially of."

As used herein, "Northern Blotting Analysis" means a technique for detecting the presence of specific RNA molecules such as the procedure disclosed by Maniatis, T., E. F. Fritsch and J. Sambrook (1982) *Molecular Cloning: P A Laboratorv Manual*, (Cold Spring Harbour Laboratory: New York), pp. 7.43–7.51, incorporated herein by reference. Briefly, RNA molecules in a sample are denatured by mixing them with an agent to prevent hydrogen bonds between base pairs so that the RNA is in unfolded, linear form. The RNA sample is then separated according to size by gel electrophoresis. The RNA sample is then transferred to a nitrocellulose filter to which the extended denatured RNA will adhere. The filter is exposed to a labeled DNA probe and subjected to autoradiography. This technique will indicate the presence as well as the quantity and size of a specific RNA in a sample.

As used herein, "RNase Protection Assay" means a technique for detecting the presence of specific RNA molecules. Briefly, a single-stranded, radioactive labeled RNA probe is synthesized. The labelled probe is mixed with an RNA sample. The probe specifically hybridizes with its corresponding RNA molecules to form double stranded hybrids. Upon digesting with RNase, the unhybridized single stranded RNA molecules and excess probe molecules are destroyed and only the double stranded hybrids are left intact. The hybrids are subsequently separated on a polyacrylamide gel and detected by autoradiography, thereby indicating the presence and amount of a specific RNA in a sample. Preferably, the procedure used is that of Ambion Inc.'s ribonuclease protection assay kit (RPA™; Ambion, Inc., Austin, Tex.), incorporated herein by reference. The RPA™ protocol involves the following steps of a) hybridization of probe and sample RNA, b) RNase digestion of hybridized RNAs, and c) separation and detection of protected fragments:

Under the RPA™ protocol, the probe and sample RNA are hybridized by the following methods: For each experimental tube, mix $^{32}$P-labeled probe (usually about 150–900 pg or $2\times10^4$–$1.2\times10^5$ cpm) with sample RNA (usually about 1–10 $\mu$g) in a 1.5 ml microfuge tube. Make 2 control tubes for every probe to be used, by mixing 2 $\mu$l yeast RNA solution (5 mg/ml yeast RNA in $dH_2O$) with the same amount of labeled probe used for the experimental tubes in the preceding step. Ethanol precipitate samples by adjusting the concentration of $NH_4OAc$ to 0.5 M and adding 2 ½ volumes of EtOH. Place tubes in −80° C. freezer for 15 min. Pellet probe and sample RNA for 15 min. at maximum speed of microcentrifuge, preferably at 4° C. Carefully remove EtOH supernatant from each tube. Resuspend each pellet in 20 $\mu$l hybridization buffer (80% deionized formamide/40 mM PIPES pH 6.4/400 mM NaOAc pH 6.4/1 mM EDTA) by thoroughly vortexing and briefly centrifuging tubes. Heat all tubes 80°–90° C. for 3–4 min. Incubate tubes submerged in 45° C. heat block or in a 42°–45° C. incubator overnight.

RNase Digestion of Hybridized RNAs under the RPA™ protocol involves the following methods: Prepare working dilutions of concentrated RNase A/RNase T1 solutions (300 $\mu$l of a mixture of 50 units/ml RNase A+10,000 units/ml RNase T1 (cloned)) in RNase digestion buffer. Typical dilution of the RNase A/RNase T1 solutions is 1:100. Remove tubes from 45° C. block or incubator and microfuge briefly if condensation is present on sides of tubes. Add 200 $\mu$l of diluted RNase solution (RNase digestion buffer and RNases) to all experimental tubes, and to one control tube of each pair of control tubes. Add 200 $\mu$l of RNase digestion buffer without RNase to the remaining control tube(s), one for each different probe used. Vortex and microfuge all tubes briefly. Incubate tubes for 30 min. at 37° C. Remove SDS solution (20% SDS) from freezer and thaw at 37° C. or 42° C., then mix together equal volumes of Proteinase K/yeast RNA solution (Proteinase K/yeast RNA in 50% glycerol) and SDS solution. Use 10 μl of each solution for each tube in the assay. Add 20 μl of the 1:1 mixture of the Proteinase K/yeast RNA solution and SDS solution to each tube. Vortex and microfuge all tubes briefly. Incubate all tubes for 15 min. at 37° C. Add 250 μl phenol/$CHCl_3$/isoamyl alcohol (25:24:1) to each tube; vortex thoroughly and microfuge for at least 1 min. to completely separate phases. Remove aqueous phases to corresponding fresh tubes. Add 625 μl 100% EtOH to each tube. Vortex tubes and store at −80° C. for 15 min.

Under the RPA™ protocol, separation and detection of protected fragments is conducted by the following methods: Prepare a denaturing polyacrylamide gel suitable for separation of protected fragments of expected size. Remove tubes from freezer and microfuge for 15 min. at mazimum speed at 4° C. Carefully remove EtOH supernatant from each tube. Resuspend each pellet in 8 μl loading buffer solution (80% formamide/0.1% xylene cyanol/0.1% bromophenol blue/2mM EDTA) by vigorous vortexing and brief microfuging. Heat all tubes for 3–4 min. at 80°–90° C. Re-vortex and re-microfuge tubes briefly. Load samples on polyacrylamide gel and run at approximately 250 volts for about 1 hour in Tris-borate buffer. Transfer gel to chromatography paper, cover with plastic wrap, and expose to X-ray film at −80° C.

As used herein, "Dot Blotting Analysis" means a technique for detecting the presence of specific RNA molecules such as the procedure disclosed by *Maniatis,* pp. 7.37–7.52, incorporated herein by reference. Briefly, an RNA sample is denatured to fully extend the RNA molecules. An amount of RNA is transferred to a nitrocellulose filter with a Dotting apparatus (IBI Inc., subsidiary of Eastman Kodak Co., New Haven, Conn.). The filter is hybridized with the radioactive labeled nucleic acid probe and subjected to autoradiography thereby indicating the presence and amount of a specific RNA in a sample.

As used herein, "Reverse Transcription-Polymerase Chain Reaction" means a technique for detecting the presence of RNA molecules such as the procedure disclosed by Innis, M. A., D. H. Gelfand, J. J. Sninsky and T. J. White, (1990) *PCR Protocols: A Guide to Method and Application,* (Cetus Corporation: Emeryville, Calif.), incorporated herein by reference; or the procedure disclosed in U.S. Pat. No. 5,213,961, Bunn, Gilliland, Blanchard and Perrin, issued May 25, 1993, incorporated herein by reference. Briefly, a pair of sequence and species specific primers corresponding to the sequence of the RNA molecule to be detected are synthesized. The primer corresponding to the 3' portion of the RNA molecule (down stream primer) is used to convert RNA into cDNA in the presence of four types of deoxynucleoside triphosphates and reverse transcriptase. The primer corresponding to the 5' portion of the RNA molecule (upstream primer) and Taq polymerase are subsequently added. The mixture is heated so that the cDNA/RNA duplex will melt to separate into single stranded molecules. When the temperature is lowered to a certain point, the upstream primer will hybridize with the cDNA and extend along the cDNA molecule to form a DNA duplex. The DNA duplex is separated into single stranded molecules upon reheating. When the temperature is again reduced, the up and down stream primers hybridize to each DNA strand respectively, extending to form new DNA duplexes. Repeating the steps of increasing and decreasing temperature results in the amplification of the specific RNA molecule. The amplified molecules can be detected with either D scan, ethidium bromide staining or autoradiography. The technique is advantageous in that it will detect the presence of an extremely small amount of a specific RNA in a sample or detect the presence of a specific RNA from an extremely limited amount of RNA sample.

Hair Specific Keratin Genes and Fragments Thereof

The applicants have isolated two human hair specific keratin genes. The complete DNA sequence of the first isolated human hair specific keratin gene has been determined by the Applicants as follows: SEQ ID NO:11. This sequence encoding the first human hair specific keratin gene has been incorporated into a bacterial phage. This phage containing the first human hair specific keratin gene has been named HLXL2-6. Phage HL-XL2-6 was deposited with the American Type Culture Collection (ATCC) in Bethesda, Md. on Aug. 25, 1993. The deposited cell line has been assigned Accession No. ATCC 75537.

As is recognized in the art, there are occasionally errors in DNA and amino acid sequencing methods. As a result, the first isolated hair specific keratin gene sequence of the present invention encoded in the deposited material, ATCC Accesion No. ATCC 75537 is incorporated herein by reference and controlling in the event of an error in the sequence found in the written description of the present invention. It is further noted that one of ordinary skill in the art reproducing the Applicants' work from the written disclosure can discover any sequencing errors using routine skill.

Portions of the second isolated human hair specific keratin gene have been sequenced by the Applicants. The sequenced portions include the following DNA sequences: SEQ ID NO:6, SEQ ID NO:7, SEQ ID NO:8, SEQ ID NO:9 and SEQ ID NO:10.

The positional order of SEQ ID NO:7, SEQ ID NO:8 and SEQ ID NO:9, relative to one another, is believed to be as follows: There is a gap of unknown base pair length between SEQ ID NO:7 and SEQ ID NO:8, and a gap of unknown base pair length between SEQ ID NO:8 and SEQ ID NO:9. Preferably the portion of the isolated human hair specific keratin gene comprising these three sequences is less than about 40 kilobases, more preferably less than about 35 kilobases. Preferably either gap of unknown base pair length is from about 1 base to about 40,000 bases, more preferably from about 100 bases to about 30,000 bases, more preferably still from about 1,000 bases to about 10,000 bases.

SEQ ID NO:10 is believed to occur between SEQ ID NO:6 and the carboxy terminus of the second isolated human hair specific keratin gene.

SEQ ID NO:6 is believed to occur between SEQ ID NO:7 and SEQ ID NO:10 of the second isolated human hair specific keratin gene.

Schematically, the positional order of the sequenced portions of the second isolated hair specific keratin gene is as follows:

SEQ ID NO:10—SEQ ID NO:6—SEQ ID NO:7—SEQ ID NO:8—SEQ ID NO:9

As used herein, "fragment" means a segment of a keratin gene of the present invention, preferably of the first or second isolated human hair specific keratin gene of the present invention, having from about 5 to about 1,500 base pairs, preferably from about 10 to about 1,000 base pairs, more preferably from about 15 to about 500 base pairs, more preferably still from about 20 to about 200 base pairs. In one embodiment of the present invention, the fragment of the first isolated human hair specific keratin gene having SEQ ID NO:11 is preferably SEQ ID NO:5. In another embodiment of the present invention, the fragment of the second isolated human hair specific keratin gene is preferably selected from the group consisting of SEQ ID NO:6, SEQ ID NO:7, SEQ ID NO:8, SEQ ID NO:9, and SEQ ID NO:10.

Either of the first or second isolated hair specific keratin genes, or fragments thereof, including those fragments specifically identified, are useful in the following assays which involve measuring the level of hair specific keratin production.

Detecting the Level of Hair Specific Keratin in a Biological Sample

The present invention additionally relates to a method for detecting the level of hair specific keratin in a biological sample, the method comprising: a) isolating the biological sample from a subject; and b) using a DNA sequence which encodes hair specific keratin, or a fragment thereof, as a marker in a biological assay to detect the level of hair specific keratin in the biological sample.

Identification of Hair Growth Regulating Actives

The present invention additionally relates to a method of identifying hair growth regulating compounds and compositions comprising:

a) treating a subject with a compound or composition of interest (e.g., a compound believed to be potentially useful for regulating hair growth);

b) isolating a biological sample from the subject; and c) using a DNA sequence which encodes hair specific keratin, or fragment thereof, as a marker in a biological assay to detect an increase in the production of hair specific keratin in the hair sample.

The present invention also relates to a method of identifying hair growth regulating compounds and compositions comprising:

a) treating in vitro material with a compound or composition of interest;

b) using a DNA sequence which encodes hair specific keratin, or fragment thereof, as a marker in a biological assay to detect an increase in the production of hair specific keratin in the in vitro hair follicle material.

Diagnostic Applications

The progression of hair loss is a complex biological process and is difficult to diagnose clinically until the thinning of hair is visibly apparent. Conversely, in bald individuals the response of a drug treatment, whether topical, parental or oral, is very difficult to ascertain until several months later. In both situations, the patient and doctor would benefit if the progression of hair loss and the effectiveness of the therapy could be monitored with a relatively inexpensive and non-invasive test.

The technique for Measuring Hair Specific Keratin Gene Expression via Reverse Transcription-Polymerase Chain Reaction, disclosed herein, (hereinafter, PCR Technique) can be utilized in diagnostic applications for early detection of hair loss and/or determination of effectiveness of hair growth regulation therapy.

a. Early Detection of Hair Loss

As used herein, "vertex region" means the region of the scalp encompassing the crown or topmost point of the vault of the skull.

As used herein, "frontotemporal region" means the region of the scalp encompassing the anterior or frontal portion of the skull; commonly referred to as "receding hairline".

As used herein, "occipital region" means the region of the scalp encompassing the back of the skull.

As used herein, "temporal region" means the region of the scalp encompassing either side of the skull above the ears, but not including the frontotemporal region.

Hair follicles progressively miniaturize with degeneration and become non-functional follicles in balding individuals. The progressive miniaturization results in a steady decrease in hair specific keratin message, detectable by the PCR Technique. Subjects concerned about hair loss but unable to visually detect thinning of the hair can have biological samples analyzed for comparison of hair specific keratin message among the areas of the scalp having a greater potential for experiencing extensive hair loss (e.g., the vertex and frontotemporal regions) and limited to no hair loss (e.g., occipital and temporal region). A large difference in hair specific keratin message would suggest that the subject is suffering from hair loss related to miniaturization of follicles and hence a disease condition (e.g., androgenetic alopecia). This early detection would allow the subject to seek treatment for the hair loss prior to visual detection of hair loss on the scalp.

Alternatively, subjects concerned about hair loss but unable to visually detect hair loss can have a biological sample isolated at an earlier date and a biological sample isolated at a later date, and analyzed for comparison of hair specific keratin message. A large decrease in hair specific keratin level of the later dated sample as compared to the earlier dated sample would suggest that the subject is suffering from hair loss related to miniaturization of follicles and hence a disease condition (e.g., androgenetic alopecia). This early detection would allow the subject to seek treatment for the hair loss prior to visual detection of hair loss on the scalp.

Such methods for detecting hair loss would comprise: a) isolating a first biological sample from a subject, b) isolating a second biological sample from the subject, c) using a DNA sequence which encodes hair specific keratin, or fragment thereof, as a marker in a biological assay to detect a difference in the production of hair specific keratin in the biological samples.

In one embodiment, the first biological sample is isolated from an area of the scalp having a greater potential for experiencing extensive hair loss, preferably an area selected from the group consisting of the vertex region and the frontotemporal region. The second biological sample is isolated from an area of the scalp having a limited to no potential for hair loss, preferably a region selected from the group consisting of the occipital region and the temporal region.

In another embodiment, the first biological sample is isolated at an earlier point in time with respect to extraction of the second biological sample. The second biological sample is isolated at a later point in time with respect to the first sample. Preferably the first and second samples are isolated from about the same region of the scalp. Preferably the second sample is isolated from about one week to about ten years after taking the first sample, more preferably from about two weeks to about five years, more preferably still from about three weeks to about one year, most preferably from about one month to about six months.

b. Early Detection of Treatment Efficacy

Clinical reports suggest many patients undergoing minoxidil treatment get frustrated and discontinue using the drug when they see no visible hair growth effect on the scalp following several months of treatment, even though they would have seen meaningful hair growth if they had continued on the drug for a few more months. The diagnostic use of the PCR Technique will allow these individuals to make a more informed decision. Patients may be asked to undergo the PCR Technique analysis. If the hair specific keratin message is detectable in a sufficient amount, discontinuation of the drug treatment would not be recommended. In contrast, if detectable hair specific keratin activity is not observed, the patient would get a prescription for a different dose regimen, or be placed on a different active for a better response. This would avoid unnecessary exposure of non-responding subjects to an ineffective treatment and, thereby, save the patient money and aggravation.

Such a method for early detection of treatment efficacy would comprise: a) isolating a first biological sample, b) treating a subject with a compound or composition known for increasing hair growth, c) isolating a second biological sample from the subject, and d) using a DNA sequence which encodes hair specific keratin, or fragment thereof, as a marker in a biological assay to detect an increase in the production of hair specific keratin in the sample. An increase in the level of hair specific keratin would indicate that the compound or composition is efficacious for that subject.

As previously stated, the isolated hair specific keratin genes, or fragments thereof, of the present invention are useful in the methods of the present invention for identifying potential hair growth compounds or efficacious compositions useful for regulating hair growth comprising such compounds. Various factors which may contribute to the efficacy of a hair growth composition may include, but are not limited to, the concentration of the active compound, penetration enhancing components, and the addition of complimentary hair growth actives.

EXAMPLE I

Isolation of the Human Hair Specific Keratin Genes

The cDNAs encoding two species of mouse hair specific keratins, type I-A1 and type II-B2 are cloned. (Bertolino, A. P., D. M. Checilal, R. Notterman, I. Sklaver, T. A. Schiff, I. M. Freed berg and G. J. GiDona, (1988) "Cloning and Characterization of a Mouse Type I Hair Keratin cDNA", Journal of Investigative Dermatology, Vol. 75, pp. 311–315; and Yu, D. W., I. M. Freedberg and A. P. Bertolino, (1990) "Complementary DNA and Deduced Amino Acid Sequences of Mouse Type II Hair Keratins", Clin. Res., Vol. 38, pp. 655A, both incorporated herein by reference). The evolutionary conservation between mouse and human genes is taken advantage of to isolate the human genes corresponding to the mouse genes coding for the mouse hair specific keratins.

1. Synthesis of Oligonucleotides

Two pairs of oligonucleotides are synthesized based upon the individual cDNA strands of the mouse cDNA. One pair (SEQ ID NO:1 and SEQ ID NO:2) is designed according to the cDNA sequence of mouse type I-A1 hair specific keratin and the other pair (SEQ ID NO:3 and SEQ ID NO:4) is designed according to the cDNA sequence of mouse type II-B2 hair specific keratin.

2. Isolation of the Fragments of Human Hair Specific Keratin Genes

Human genomic DNA is obtained from a commercial supplier (Clontech Laboratories, Inc., Palo Alto, Calif.). The above two pairs of oligonucleotides are used to specifically amplify their human counterparts from the human genomic DNA through the use of the standard polymerase chain reaction (PCR) technique as disclosed by Innis, incorporated herein by reference. Briefly, each pair of oligonucleotides are mixed with the human genomic DNA. The oligonucleotides hybridize with their corresponding human DNA. The hybridized probe acts as a primer for DNA chain synthesis which begins upon the addition of four types of deoxynucleoside triphosphate (dATP, dCTP, dGTP and dTTP) and Taq polymerase. When synthesis is complete, the whole mixture is heated further to melt the newly formed DNA duplexes. When the temperature is lowered again, another round of synthesis can take place. This cycle of synthesizing and remelting is repeated to specifically amplify the sequences of interest. Two human hair specific keratin gene fragments are obtained by the PCR technique, SEQ ID NO:5 and SEQ ID NO:6.

3. Determining the Nucleotide Sequence of the Keratin Fragments

Both SEQ ID NO:5 AND SEQ ID NO:6 are subcloned into plasmid vector pGEM 3Z. (Promega Corp., Madison, Wisc.). The nucleotide sequence of both fragments is determined by the standard dideoxynucleotide sequencing technique disclosed by Maniatis, pp. 13.713.74, incorporated herein by reference.

4. Isolation of Complete Human Hair Specific Keratin Genes

SEQ ID NO:5 and SEQ ID NO:6 are used as probes to screen a genomic library to identify and isolate the human hair specific keratin genes respectively comprising those DNA sequences. The procedure used is as disclosed by *Maniatis,* pp. 1.90–1.104, incorporated herein by reference.

EXAMPLE II

Isolation of a Polvnucleic Acid Comprising a Human Hair Specific Keratin Gene SEQ ID NO:6 is used as a probe to screen a genomic library (Clontech, Emeryville, Calif.) to identify a polynucleic acid comprising a human hair specific keratin gene comprising SEQ ID NO:6, following the procedure disclosed in Example I, part 4. SEQ ID NO:6 is $^{32}$P labeled and the probe is hybridized to a nitrocellulose filter to which the genomic clones are fixed. The positive hybridization signal is identified by autoradiography. After screening, a positive clone is identified hybridized to SEQ ID NO:6. The clone comprises DNA sequence SEQ ID NO:7, SEQ ID NO:8 and SEQ ID NO:9 wherein there is a gap of unknown base pair length between SEQ ID NO:7 and SEQ ID NO:8, and a gap of unknown base pair length between SEQ ID NO:8 and SEQ ID NO:9; as well as DNA sequence SEQ ID NO:10. Digestion of the isolated clone with EcoRI produces several fragments, one such fragment having SEQ ID NO:10, another such fragment having SEQ ID NO:7, SEQ ID NO:8 and SEQ ID NO:9 with gaps as described above.

EXAMPLE III

Measuring Hair specific keratin Gene Expression via Reverse Transcription-Polymerase Chain Reaction As discussed above, several biological assays employing a DNA sequence, or fragment thereof, which encodes for hair specific keratin as probes, may be used to measure the degree of hair specific keratin gene expression in a sample. In one embodiment of the present invention, the biological assay involves the Reverse Transcription-Polymerase Chain Reaction (RT-PCR), as disclosed by Innis, incorporated herein by reference, with the following modifications.

1. Synthesis of PCR primers

A pair of primers are synthesized according to SEQ ID NO:5. Primer #1 is made up of base pairs (b.p.) 53 to 75 of SEQ ID NO:5 (upstream primer). Primer #2 is made up of b.p. 1140 to 1165 of SEQ ID NO:6 (downstream primer).

2. Isolation of total RNA from Hair Samples

Hair is plucked from a subject (approximately 10 to 20 strands). The total RNA is isolated from the hair sample using an RNAzol Kit™ (Tel-Test, Inc., Freindswood, Tex.). The RNAzol Kit™ comprises reagents useful for isolating total RNA from a tissue or cultured cells. The major components of the RNAzol Kit198 comprise: guanidinium thiocyanate, phenol and buffer. The RNAzol Kit™ procedure is incorporated herein by reference, except that the hair roots from the plucked hairs are excised and placed into 250 μl of RNAzol solution followed by vortexing for 20 seconds and subsequently removing undissolved debris. Hair samples are taken from the subject before and after treatment with a potential hair growth regulating compound.

3. Amplification of Hair Specific Keratin RNA

Primer #2 is used for carrying out reverse transcription. The primer is mixed with total RNA, four types of deoxynucleoside triphosphate (dATP, dCTP, dGTP and dTTP) and reverse transcriptase. Reverse transcription is carried out at 42° C. for forty-five minutes. Upon the completion of reverse transcription, PCR is initiated by the addition of primer #1 and Taq polymerase. The reaction is performed under a temperature combination of 60° C. and 95° C. for 25 cycles. The amplified hair specific keratin product can be detected by gel electrophoresis and visualized under UV light after being stained with ethidium bromide.

4. Generate Control RNA for the Quantitative PCR

In order to apply the RT-PCR technique for the purpose of accurately quantitating hair specific keratin RNA level, an external control RNA is necessary. Incorporation of a control RNA to the reaction will minimize the variations which may occur during the PCR amplification process thereby increasing the accuracy of the quantitation results. Criteria for selecting a control RNA include: 1) the control RNA should use the same pair of primers as the hair specific keratin RNA in the process of RT-PCR, and 2) the size of amplified end products of control RNA should be different from that of the hair specific keratin RNA.

For purposes of this Example Ill, a control RNA is generated by in vitro transcription, a standard protocol of which is disclosed by Promega Corp., Madison, Wisc., in their In Vitro Transcription Kit™, incorporated herein by reference. The major components for in vitro transcription comprise: T7 or SPG polymerase; dATP, dCTP, dGTP and dTTP; RNase inhibitor; and buffer for the reaction. The template used for in vitro transcription is a derivative of the plasmid containing SEQ ID NO:5 from Example 1, part 3. This control RNA contains an almost identical sequence to that of SEQ ID NO:5 except base pairs 347 to 715 are removed.

5. Quantitation of Hair specific keratin RNA Level

Prior to RT-PCR amplification, an equal amount of control RNA is added to each sample (pre- and post- hair growth regulating compound treated samples). RT-PCR is carried out by following procedure 3, above, except 32P dCTP is added to the reaction. The control RNA and hair specific keratin RNA are co-amplified together. Upon completion of the PCR amplification, the end products (both control and hair specific keratin RNA) are separated by polyacrylamide gel electrophoresis and the signals are quantified with Beta-Scope (Betagen Inc., Waltham, Mass.). The amount of hair specific keratin RNA is determined by its relative signal intensity to the control RNA. The level of hair specific keratin RNA before and after treating with potential hair growth regulating compounds are compared. An increase in hair specific keratin RNA level, as compared to the control, is suggestive of a compound's use for regulating hair growth. Preferably there is an increase in specific keratin RNA level of 5%, more preferably 10%, more preferably still 25%.

The invention has been described herein with reference to certain preferred embodiments and examples. Obvious variations may appear to those skilled in the art. Therefore, the invention is not to be considered limited thereto but only by the claims which follow.

SEQUENCE LISTING

```
(1) GENERAL INFORMATION:

   (iii) NUMBER OF SEQUENCES: 11


(2) INFORMATION FOR SEQ ID NO:1:

     (i) SEQUENCE CHARACTERISTICS:
          (A) LENGTH: 21 base pairs
          (B) TYPE: nucleic acid
          (C) STRANDEDNESS: single
          (D) TOPOLOGY: linear

    (xi) SEQUENCE DESCRIPTION: SEQ ID NO:1:

CTAGAGCGTC AGAACCAGGA G                                          21


(2) INFORMATION FOR SEQ ID NO:2:

     (i) SEQUENCE CHARACTERISTICS:
          (A) LENGTH: 21 base pairs
          (B) TYPE: nucleic acid
          (C) STRANDEDNESS: single
          (D) TOPOLOGY: linear

    (xi) SEQUENCE DESCRIPTION: SEQ ID NO:2:

AAGCGGACAA GGGAGGGCCA G                                          21
```

-continued (2) INFORMATION FOR SEQ ID NO:3:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:3:

GAATTCCAGG AGGTGATGAA CTCC 24

(2) INFORMATION FOR SEQ ID NO:4:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:4:

TCAAGAGGGC GCACACACGC C 21

(2) INFORMATION FOR SEQ ID NO:5:

(i) SEQUENCE CHARACTERISTICS:
(A) LENGTH: 1195 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:5:

CTAGAGCGTC AGAACCAGGA GTACCAGGTG CTGCTGGATG TGCGTGCCCG GCTGGAGTGT 60

GAGATCAACA CATACCGGAG CCTGCTGGAG AGCGAGGACG CAAGTGAGTA CATGGCAGAC 120

GTGTTTGATG AAATGATGCA CGTGTGACTG TAACAGTTGG ACACCATGCA AATATTGCAT 180

ACCTTGGAAA GGAAATTATG CCTTCACACT AGACATGCTC AAACAGAACT CAGACAACAT 240

AATATGGCCA TCATTTAAAA CATAAATGGT TTGGTAGCAA GAGTTGTTTG ATGTACAAAC 300

TGAAATTCGC ACTGCCAAGT CTTTGCATTC TAGTATGATA ATATGCATGA CTGCATGATA 360

TGTGATCAAG CCTTGTTTTT ACAATACTGT ATTGCCTAGT GGGTACATTC CCATAGGCTA 420

CCTGATTTGA TCTTATAATT ACACCAGGGG GCTGGATCAG TATTCCCTCC ATTCTACAGG 480

AAAGTAAACT GGGGCTTGGA GAAGGTAAAT GACTCACCCC ATGTCATCAG TTTGGCATGA 540

ATGGATTTGA GAGTAGACAT CAGAGTTTCA GAGTTTCTGT CTACCTTGGT GCTCTATGGC 600

AGGGAGACCA TTAACAATTT GAGTTAGTTA TCTTTGTAGC AGGGGAGTCT GTGCCTTTTC 660

TGTTCTAGGC CATGGCAAGT CCCTTGACCC AGGCATTCTT ACCCTTGGGG ATATCTCTGG 720

CATATGATTT TAAAATTGCC CTTAACTCAC TTTTCCACAT CACTTTTGTC TCCAGTCTGC 780

CCAGCAATCC CTGTGCCACG ACCAACGCGT GCAGCAAGCC CATCGGACCC TGTCTCTCCA 840

ATCCCTGTAC CTCTTGTGTC CCTCCTGCCC CCTGCACACC CTGTGCCCCA CGCCCCCGCT 900

GTGGGCCCTG CAATTCCTTC GGGCCTGCAA GGTAGGGAAT GCCAGAGGAG CAAGGATGCA 960

GGGCCCAGGA CTGGAGAGCT GTGACCTGGC TCTGGTTCAA CAAAAGGGGC CTGAAAACAT 1020

CATTTGCATG GCTGGAGTTG CCCGCGTAAG GCGCCCAAGA AACTCACCCA AAGCCTGTAG 1080

CCTCCCCAAC TACTCCAGAC TGTCCTGCTC ACCCATTTCC TTCCTGGGGG TCTGTTCCTT 1140

CCTATGCTCA CCCAGAGAAC TCTCTGATGT CGCACTGGCC CTCCCTTGTA AGCTT 1195

-continued (2) INFORMATION FOR SEQ ID NO:6:

(i) SEQUENCE CHARACTERISTICS:
(A) LENGTH: 827 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

```
GAATTCAGGA GGTGATGAAC TCCAAGCTGG GCCTGGACAT CGAGATCGCC ACCTACAGGC     60

GCCTGCTGGA GGGCGAGGAG CAGAGCTGGG TCCAACCAAG GGTGGCCCAG AACCACCCTT    120

CCCCATCCCT GGCACAAGCC TACCCTTGGC CTTGCTGAGC AATGGCCAGG GCTCTGGGGG    180

AAAAAAATAT TATTATTCAC TTCCGGTGTG GGGAGGGCGG TGTGTGAGTT TGTCTGAGGC    240

AAGCTGTTCC CTCAGACTCT GTTCTTAATT GACCAGTTGT GGACCCTACC CTATGAACTG    300

GGGAGCTTTT TCAGCCACTC TGGGGCAGTC ACTAATGTTG CCTTTTTCTC TTTCGCCCTC    360

AGGCTATGTG AAGGCATTGG GGCTGTGAAT GTCTGTGAGT ATTTGGGGTC CAGTGTGGAC    420

AGATTTACTA ACTACCTGTG ATGGAGGGGA GAGTTTGGAA AAAGGAGTGT TACTGAGATT    480

GAATATAAAA GAGTGGGCTG GCATCACAAC AGGAGGGATT TGGGGTCATA CATCCAAAAG    540

ACCCCAGCTC TTGGACTAGA TGGACCTAGA ATTGTCCACA AAGATGCCTC TGACTTTTCA    600

TACCAGAGCT GAGGTCTTGG GCAGGGGCGG TTGTCAGGAG GGCAGGATGG CTTGCCCTTC    660

AGAATTTTGA CTCAGCTTCG GGGTTCACAG GTGTCAGCAG CTGGCGGGGC GGGGTCGTGT    720

GCGGGGACCT CTGCGTGTCA GGCTCCCGGC CAGTGACTGG CAGTGTCTGC AGCGCTCCGT    780

GCAACGGGAA CGTGGCGGTG AGCACCGGCC TGTGTGCGCC CTCTAGA                  827
```

(2) INFORMATION FOR SEQ ID NO:7:

(i) SEQUENCE CHARACTERISTICS:
(A) LENGTH: 291 base pairs
(B) TYPE: nucleic acid
(C) STRANDEDNESS: single
(D) TOPOLOGY: linear (xi) SEQUENCE DESCRIPTION: SEQ ID NO:7:

```
GAATTCTAGC TCTGCCACTC TCTAGCTGTG TAAACTCAGG CAATTACTTA GCCTCTATGT     60

ACCTCATTTC ATGATTTCTA AAATGAAGAT AATAATAGTA CCCACCTCAT AAAGTTGTAA    120

AGATTAAAAG AGTTAATCCA TGTAAATCAC TGAGAACTAA GCCTGGCACA CTCTAAGTGT    180

GTAATCATAT TAGTTGTTGT TGTTGTTGCT GCTGATGCTG CTGCTGCAGA CGTATCAACA    240

GCATTGATGG GATATACTCA TCACATGCCT AAGCCATCTG TGTCCAGTTT T             291
```

(2) INFORMATION FOR SEQ ID NO:8:

(i) SEQUENCE CHARACTERISTICS:
(A) LENGTH: 376 base pairs
(B) TYPE: nucleic acid
(C) STRANDEDNESS: single
(D) TOPOLOGY: linear (xi) SEQUENCE DESCRIPTION: SEQ ID NO:8:

```
TGCTGGAGGG CAAGGAGCAG AGGTGGGTCC AACCAAGGGT GGCCCAGAAC CACCCTTCCC     60

CATCCCTGGC ACAAGCCTAC CCTTGGCCTT GCTGAGCAAT GGCCAGGGCT CTGGGGGAAA    120

AAATGTGGAC CCTACCCTAT GAACTGGGGG AGCTTTTTCA GCCACTCTGG GGCAGTCACT    180

AATGTTGCCT TTTTCTCTTT TCGCCCTCAG GCTATGTGAA GGCATTGGGG CTGTGAATGT    240
```

-continued

```
CTGTCAGTAT TTGGGGTCCA GTGTGGACAG ATTTACTAAC TACCTGTGAT GGAGGGCAGA    300

GTTTGGAAAA AGGAGTGTTA CTGAGATTGA ATATAAAAGA GTGGGCTGGC ATCACAACAG    360

GAGGGATTTG GGGTCA                                                    376
```

(2) INFORMATION FOR SEQ ID NO:9:

(i) SEQUENCE CHARACTERISTICS:
(A) LENGTH: 295 base pairs
(B) TYPE: nucleic acid
(C) STRANDEDNESS: single
(D) TOPOLOGY: linear (xi) SEQUENCE DESCRIPTION: SEQ ID NO:9:

```
TACCGACACA ACCCTAATGA TACACCTTGC AGATGAAGAA GCCAGAACTC AGAGGCACTC     60

AATAATTGGG GCAGGGTCAC CCACTTAGTT GGGTGGTTCA TCTGGGGTTT AAGCCCTGTG    120

TGTGTCGCTA GTGCTGCATT TCACTAAACT GCAGCTGTCT CTCAGAAAAC ATCTCATGCA    180

TATCTGCAAA CTGATGGATC ATGAAAATCA GATTCACCAA TCACTCAAAG CTTGAGGCAA    240

CATCACCCAT TGCTTTGGTA GGGAAGACTC ATGCCTGAGT AATTTATTGG AATTC         295
```

(2) INFORMATION FOR SEQ ID NO:10:

(i) SEQUENCE CHARACTERISTICS:
(A) LENGTH: 856 base pairs
(B) TYPE: nucleic acid
(C) STRANDEDNESS: single
(D) TOPOLOGY: linear (xi) SEQUENCE DESCRIPTION: SEQ ID NO:10:

```
GAATTCCATC AGGGGTGGCT GAGAGACCTT GGTTTGATTC TAGCTTTTAC AGGAGAATTT     60

GTTCTTTTCA GTCCACTCAC TTCTGGTCTC TTAATATTCT TAATAATTTC TAGTGCCCAG    120

AAGGGTAGGG GTGGGGGACT CCCATTTCTG CTGTATTTTC TGGGCCTTGG ACTGGAAGTT    180

TAGAGATTCA CTCCGGTTTA AAGATGTATG TTCAGGGAGT CACCTTGGCC CATAGTGGGC    240

GTGAGCTGTC ATCTTCCCCT TCCCCTACCT CATCAGTGTC AACTTAATAC TTCCATGCAT    300

GAAGGAGCTG AATGGCCCTG GTAACCACGG AGGTTTCTCT CTGTACTTGC AATCTCTGAT    360

CACAGATATC AATGTAATAA GAGGTTGGCC ATAAGAGGCC CTGATCCCTA GAGGGACTTC    420

TACTTTACAT TCTGCAAAAA GAATAACACT AATGATAAAA AATAGAGTGA TAATTTTGTG    480

GCATGCACCA TCTAAACCTT TTACGTATAT GAAATCCTTT AACTCATCAG CTTATGAGGT    540

GGTTGCCCTT TCTATCATCC TCATTTTGGA GGTGTGGAAA CAGGCAGCAG AGAGGGAAAT    600

ACATTGCCCA ACCCACTCAC CTAGGAAGGA CCAGGCCCGA GCTTGGGGCC CAGGCAGTCT    660

GGCTGGAGTC CGTGTCCCCC CTCTATGCCA CATCATCTTG CTATGTGCTC TTTTCTGTCT    720

TTGAGAAAAA TGTATCAGCT GTGGCAGGTC TCCAAAACCC CAGAGTGATG CCATTTAAAA    780

AAAAAAAAAG AAAGCCAACA TCAAAGGCTT TTTGAAACTT TAAATCATAT TCATGTATTC    840

ACCTCTTAAA GAATTC                                                    856
```

(2) INFORMATION FOR SEQ ID NO:11:

(i) SEQUENCE CHARACTERISTICS:
(A) LENGTH: 3914 base pairs
(B) TYPE: nucleic acid
(C) STRANDEDNESS: single
(D) TOPOLOGY: linear (xi) SEQUENCE DESCRIPTION: SEQ ID NO:11:

-continued

```
ACAGCTCTGT GGCTTGGAGA ATTTAGACTC TGTCTTCAGC CAGGCACTCC CTCCCTCCCT     60
CCCAGCACTA TGCCCTACAA CTTCTGCCTG CCCAGCCTGA GCTGCCGCAC CAGCTGCTCC    120
TCCCGGCCCT GCGTGCCCCC CAGCTGCCAC AGCTGCACCC TGCCCGGGGC CTGCAACATC    180
CCCGCCAATG TGAGCAACTG CAACTGGTTC TGCGAGGGCT CCTTCAATGG TAGCGAGAAG    240
GAGACTATGC AGTTCCTGAA CGACCGCCTG GCCAGCTACC TGGAGAAAGT GCGTCAGCTG    300
GAGCGGGACA ACGCGGAGCT GGAGAACCTC ATCCGGGAGC GGTCTCAGCA GCAGGAGCCC    360
TTGCTGTGCC CCAGTTACCA GTCCTATTTT AAGACCATTG AGGAGCTCCA GCAGAAGGTG    420
AGCGGCATTG CTGTCATCTC CAAGCAAGAG AGTTTGCTGT GATTCTGTCT GTGATAGAGA    480
AGTGTGTTTC TTGCTTCTGT GCTGTCATAA TTCTTGCTTC CTCTTTTATT TCAAAATGGC    540
TTAAGTCATT TTTAAAAAGT TGATGATTTC ATATTTATTT TCAGTCCTCA CTAAGCCACC    600
TCTCACTCCC CAGATCCTGT GTACCAAGTC TGAGAATGCC AGGCTTGTGG TGCAGATCGA    660
CAACGCCAAG CTGGCTGCGG ATGATTTCAG AACCAAGTGA GTTGTTCGGA ATTTGCACTA    720
GTGTCAATTG CTTCTGTTTA ATCTTTAAAG AAAAGGGATT TCCATCTGAA AACAGATCTA    780
CCCACTTGTT GTGAAGGATT CTGCAGAGGA CTGGGGAGAA CCAAGCAAAG AAATGCAAAA    840
ATGGATGAGG ACTCACATCA ATCTGTTTGT TTTGGGATGA ATATTGGGTA TTGATGGAGC    900
CTCCAGAAAC CTCTGTCTCC TGGGCCTATT CATTACAGAA AGTGGAAAGA TAAGGCACAT    960
GAGGTTATCA AAAATCATTC CTGTGAGTCT TGAAGATCTA CCAGGTAGTA CTCTGACCCT   1020
GTCCTTGCGC AGGTACCAGA CCGAGCTGTC CCTGCGGCAG CTGGTGGAGT CGGACATCAA   1080
CGGTCTGCGC AGGATCCTGG ATGAGCTGAC CCTGTGCAAG TCCGACCTGG AGGCCCAGGT   1140
GGAGTCCCTG AAGGAGGAGC TGCTCTGCCT CAAGAGCAAC CATGAGCAGG TGAGACTAGA   1200
AATGAGAAAT GCACAAACCT GTCTCAGCCT CTGGCTCAGG GTTGCTTTAG TGATTTGGGG   1260
CAGCAGAATG CAGAGTATGA GTACAAGACT GAGGGTTTCC TTTGAAAACA TCACGGTAAG   1320
AGAAAAATTG GAGAGAGATA AGACCTGTTC ATGTTCCCAG ACAGGAAACA TCTTTCACTT   1380
TAAACTAGCA CATTATTTGA GTTGCCCGGA GCAGCTCCAT GTGCTTGCAG TTGATCAATA   1440
GTTGTAGAAT GAGTCCTAGC ATTGCAGTGT TATTGCTTTG TAAAGTCTTT TTTTTTTTTT   1500
TTTGGCAAAG GCCAAGAAAA AAAATATCAA ACCTTATAAA TGTGAGTCTC TACTCTTTCA   1560
AAGTATTGGT GAAGAGTGTT TGTGAGATTC TTCCTCTCTC TTGGGAGGGG CCATGACATG   1620
CTCTTACCTC TTACTTGACA GCAAGAGTTT TTTGATATAT GGTCTGAAAT TGCACAGCCT   1680
ATTTTTTTTG GCATTCTGAG GTCCTCACAG CCAATTGTAA ACTGGGAAAG TTGAATATCA   1740
ATTAGTTCAT CCTTCAGTGG CATCCAAGCA AACTTTTGGG ATTTTTTTCT GAAGCCAAGT   1800
GCCATGGCAC AGCAGATGGT GGGGAGGGGG CTATGCCACA TGGAGTGCCT TGAGCTGTCA   1860
CAAACTGCTC CACTCAAAGT TTCTTTTCCG AGAAAATAGA CTAACAGGGT TTCAACAAGC   1920
AATGCCATTC CTTAGAGTTC ATTCTTTGCT GAGCATAGTA ACTCTTGTAT TTTCTGCATC   1980
CATAGGAGGT CAATACCCTG CGCTGCCAGC TTGGAGACCG CCTCAATGTG GAGGTGGATG   2040
CTGCTCCCAC TGTGGACCTG AATCGGGTGC TGAACGAGAC CAGGAGTCAG TATGAGGCCC   2100
TGGTGGAAAC CAACCGCAGG GAAGTGGAGC AATGGTTCAC CACGCAGGTG GGCATCTAAG   2160
CACGTGGCCC CTCAGGACCC AAGGCCCCCC AGGGCCCCGG AGGCAGGGTC TGATCCTTTC   2220
TCCCCTTGGG TGTTTCAGAC CGAGGAGCTG AACAAGCAGG TGGTATCCAG CTCAGAGCAG   2280
CTGCAGTCCT ACCAGGCGGA GATCATCGAG CTGAGACGCA CAGTCAACGC CCTGGAGATC   2340
```

-continued

```
GAGCTGCAGG CCCAGCACAA CCTGGTGTGT ATTGTTCAGA CCTGCTGGTG AGCGACGGGA   2400
ACTTGGGAGG CAGAGTCCCG GGGATGTGCT TGGGGCCACA CACTCTCCTT AGCTCTTGGA   2460
GCTTGTGACT TCCTTGTAAT CCTGTGAAGA AACCCTTTGA AGGAGCAGCT CTCTGACATT   2520
CCCAATCTTC TCCACCACAG CGAGACTCTC TGGAAAACAC GCTGACAGAG AGTGAGGCCC   2580
GCTACAGCTC CCAGCTGTCC CAGGTGCAGA GCCTGATCAC CAACGTGGAG TCCCAGCTGG   2640
CGGAGATCCG CAGTGACCTG GAGCGGCAGA ACCAGGAGTA CCAGGTGCTG CTGGATGTGC   2700
GTGCCCGGCT GGAGTGTGAG ATCAACACAT ACCGGAGCCT GCTGGAGAGC GAGGACTGCA   2760
AGTGAGTACA TGGGCAGACG TGTTTGATGA AATGATGCAC GTGTGAGTGT AACAGTTAGA   2820
CACCATGCAA ATATTGCATA CCTTGGAAAG GAAATTATGC CTTCACACTA GACATGCTCA   2880
AACAGAACTC AGACAACATA ATATGGCCAT CATTTAAAAC ATAAATGGTT TGGTAGCAAG   2940
AGTTGTTTGA TGTACAAACT GAAATTGCAC TGCCAAGTCT TTGCATTCTA GTATGATAAT   3000
ATGCATGACT GCATGATATG TGATCAATGC CTTACTTTTT ACAATACTGT ATTGCCTAGT   3060
GGGTACATTC CCATAGGCTA CCTGATTTGA TCTTATAATT ACCACCAGGT GGGCTGGATC   3120
AGTATTCCCT CCATTCTACA GGAAAGTAAA CTGGGGCTTG GAGAAGGTAA ATGACTCACC   3180
CCATGTCATC AGTTTGGCAT GAATGGATTT GAGAGTAGAC ATCAGAGTTT CAGAGTTTCT   3240
GTCTACCTTG GTGCTCTATG GCAGGGAGAC CATTAACAAT TTGAGTTAGT TATCTTTGTA   3300
GCAGGGGAGT CTGTGCCTTT TCTGTTCTAG GCCAGGTCAA GTCCCTTGAC CCAGGCATTC   3360
TTACCCTTGG GGATATCTCT GGCATATGAT TTTAAAATTG CCCTTAACTC ACTTTTCCAC   3420
ATCATTCTTT TGTCTCCAGT CTGCCCAGCA ATCCCTGTGC CACGACCAAC GCGTGCAGCA   3480
AGCCCATCGG ACCCTGTCTC TCCAATCCCT GTACCTCTTG TGTCCCTCCT GCCCCCTGCA   3540
CACCCTGTGC CCCACGCCCC CGCTGTGGGC CCTGCAATTC CTTCGTGCGC TAGAACCTAG   3600
GGAATGCCAG AGGAGCAAGG ATGCAGGGCC CAGGACTCCA GAGCTGTGAC CTGGCTCTGG   3660
TTCAACAAAA GGGGCCTGAA AACATCATTT GCATGGCTGG AGTTGCCCGC GTAAGGCAGC   3720
CAAGAAACTC ACCCAAAGCC TGTAGCCTCC CCAACTACTC CAGACTGTCC TGCTCACCCT   3780
TTCCTTCCTG GGGGTCTGTT CCTTCCTATG CTCACCCAGA GAACTCTCTG ATGTGCCAGT   3840
GGCCCTCCCT TTTAACCTCC TAATAAATAT CATTTCCTTG GCAAAGCAGA TGCCTTTTTC   3900
ATTTGTATTC ATTT                                                     3914
```

What is claimed is:

1. An isolated human hair specific keratin gene or fragment thereof having a DNA sequence selected from the group consisting of a) SEQ ID NO:11; and b) a DNA sequence comprising the following DNA sequences:

i) SEQ ID NO:6 ii) SEQ ID NO:7 iii) SEQ ID NO:8 iv) SEQ ID NO:9, and v) SEQ ID NO:10.

2. The human hair specific keratin gene, or fragment thereof, of claim 1 wherein the gene has the DNA sequence SEQ ID NO:11.

3. The human hair specific keratin gene, or fragment thereof, of claim 1 wherein the gene has the DNA sequence comprising the DNA sequences:

a) SEQ ID NO:6 b) SEQ ID NO:7 c) SEQ ID NO:8 d) SEQ ID NO:9, and e) SEQ ID NO:10.

* * * * *